US006766041B2

(12) United States Patent
Golden et al.

(10) Patent No.: US 6,766,041 B2
(45) Date of Patent: Jul. 20, 2004

(54) RETINAL VASCULATURE IMAGE ACQUISITION APPARATUS AND METHOD

(75) Inventors: Bruce L. Golden, Fort Collins, CO (US); Bernard E. Rollin, Fort Collins, CO (US); Ralph v. Switzer, Jr., Fort Collins, CO (US); Carlton R. Comstock, Jr., Eaton, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 645 days.

(21) Appl. No.: 09/753,973

(22) Filed: Jan. 3, 2001

(65) Prior Publication Data

US 2003/0048929 A1 Mar. 13, 2003

Related U.S. Application Data (63) Continuation of application No. PCT/US99/15337, filed on Jul. 7, 1999.
(60) Provisional application No. 60/092,445, filed on Jul. 10, 1998, and provisional application No. 60/092,213, filed on Jul. 9, 1998.

(51) Int. Cl.[7] ............................................. G06K 9/22
(52) U.S. Cl. ...................... 382/117; 340/5.53; 340/5.83
(58) Field of Search ................................ 382/115, 116, 382/117, 110; 356/71; 340/5.52, 5.82, 5.53, 5.83, 573.2

(56) References Cited

U.S. PATENT DOCUMENTS

| 4,109,237 A | | 8/1978 | Hill | 340/146.3 E |
| 4,620,318 A | | 10/1986 | Hill | 382/2 |
| 5,457,747 A | * | 10/1995 | Drexler et al. | 713/186 |
| 5,668,621 A | * | 9/1997 | Nanjo | 351/206 |
| 5,982,555 A | * | 11/1999 | Melville et al. | 359/630 |
| 6,038,333 A | * | 3/2000 | Wang | 382/118 |

FOREIGN PATENT DOCUMENTS

| EP | 0 122 961 A2 | 10/1984 | A61B/3/12 |
| EP | 0 758 752 A1 | 2/1997 | G01S/13/87 |
| EP | 0 821 912 A2 | 2/1998 | A61B/5/117 |
| WO | WO 96/17545 | 6/1996 | A61B/3/10 |
| WO | WO 97/46979 A1 | * 12/1997 | G07C/9/00 |

OTHER PUBLICATIONS

For Background Reference Only http://www.medjhu.edu/wctb/coms/patient/photog/fundus.htm, "Ophthalmic Diagnostic Photography Ocular Fundus Photography", COMS Diagnostic Photography, 1996, The Collaborative Ocular Melanoma Study.

For Background Reference Only http://www.eri.harvard-.edu/htmlfiles/eyeagram.html, "Diagram of the Eye and Glossary of Terms".

* cited by examiner

Primary Examiner—Brian Werner
(74) Attorney, Agent, or Firm—Macheledt Bales & Heidmiller LLP (57) ABSTRACT

The present invention creates a permanent record of an animal through a series of steps including, preliminarily acquiring an image of the retinal vasculature of the animal of interest; digitizing that image if the image is not a digital image; analyzing the image to determine if the image is satisfactory for further analysis; storing the image; and analyzing the image for unique anatomical landmarks. The image and data gathered therefrom may be stored in a database for later retrieval and comparison against other images. The data gathered from the image may be compared against other stored data in the database to determine the identity of the animal. Preferably, the system would also include a global positioning system ("GPS") device which would simultaneously time and date stamp the acquired image as well as stamp the image with the location where the imaging took place by recording the latitude and longitude of that location.

25 Claims, 4 Drawing Sheets

RETINAL VASCULATURE IMAGE ACQUISITION APPARATUS AND METHOD

This application is a continuation of PCT/US99/15337, filed on Jul. 7, 1999 and published as WO 00/02480 A1 on Jan. 20, 2000, which claims priory to U.S. provisional applications 60/092,445, filed on Jul. 10, 1998, and 60/092,213, filed on Jul. 9, 1998

BACKGROUND OF THE INVENTION

1. Field of the Invention

The present invention is directed generally to an apparatus and method for creating a record that can be used to identify an animal using biometric information gathered from the animal. More specifically, the present invention is directed to an apparatus and method for creating a record that can be used to identify an animal using biometric information gathered from the eye of the animal.

2. Description of the Related Art

The issue of animal identification is as old as the domestication of animals by humans. Hot iron branding, for example, harks back to ancient Egypt. Until very recently, obvious and ancient methods of animal identification sufficed for social needs. Cattle in western United States range lands, for example, are still branded and companion animals, e.g., dogs and cats, are still tagged.

The advent of major new problems in various animal industries has accelerated the demand for new methods of identification. Most profound, perhaps, is the issue of food safety in the meat industry, particularly with respect to cattle. The emergence of dramatic new diseases carried in meat animals, most notably Bovine Spongiform Encephalopathy ("BSE" or "mad cow disease") and Johnne's disease, has generated a demand for individual animal identification that allows trace-back of each animal from current location (e.g., slaughterhouse) to birthplace. This concern carries over to other diseases such as brucellosis and tuberculoses, and also to toxicants and pollutants such as lead, PCBs, estrogen-mimicking compounds, and the like.

Apart from food safety concerns, conclusive and permanent identification of animals thus allowing for trace-back is important to animal related industries. Specifically, the cattle, pig, and sheep industries would benefit from the ability to trace these animals throughout their lives for numerous reasons, for example to determine proper title to the sold or purchased animal, to evaluate breeding operations, and to inventory herd animals, among others. These issues would be especially relevant to those involved in the raising and breeding of registered animals. Breeders of other animals, for example, cats and dogs would benefit from the ability to track animals, particularly registered animals, for title and genetic purposes. As aquaculture develops the need for conclusive and permanent fish identification would be important for the same reasons as for the cattle industry. Veterinary medicine would benefit from the ability to positively identify the animal to be treated, thus assisting in rendering proper treatment to the animal. An additional benefit could be in facilitating the tracking of veterinary medical records. In the future, a conclusive and permanent means of identification could be important in order to differentiate genetically identical clones in all species.

In animal research, the animals (e.g., dogs, cats, mice, rats, pigs, primates, and the like) must be identified for record-keeping purposes. And, in the case of dogs and cats, proper identification is required to prove that the animal in the laboratory is not a kidnapped pet.

Accordingly, a conclusive means of identifying animals is needed. Numerous methods have been used in order to identify animals, all with various shortcomings. Hot iron branding has been used for centuries and is costly to the cattle industry in lost hide value. Moreover, it is painful to the animals. Freeze branding works only on dark hided animals. In addition, freeze branding is likewise painful to the animal and decreases the hide value. Tattooing is labor intensive, alterable, and difficult to read. Tattooing is likewise painful to the animal. Tags placed in the ears and other places on the animals are easily lost. Tags are easily removed and can be falsified.

Cutting the dewlaps and ear notching are both possibly alterable and painful to the animal. Using paint to mark an animal is non-permanent and possibly alterable. Microchips, whether implanted or in ear tags, are potentially alterable and expensive. Additionally, when implanted, microchips can migrate within the animal making them difficult to relocate and are not presently approved by the Food and Drug Administration ("FDA"). Moreover, at present, microchips have not been standardized, and thus, the proper reader may not be available to evaluate the information on the microchip implanted in the animal. Ear tags containing microchips suffer from the same drawbacks as regular ear tags in addition to the drawbacks relating to microchip usage. DNA testing is very expensive and requires a substantial amount of time to acquire the results. Furthermore, DNA testing would be unable to distinguish clones as they will have the same DNA. Considering the large number of animals that, for example, would be passed through a feedlot in a given period of time, DNA testing is not timely enough for trace-back purposes.

SUMMARY OF THE INVENTION

The present invention provides an apparatus and method which can be used to create a record which provides a conclusive and permanent means for identifying virtually any species of animal using biometric information gathered from the animal. The method of the present invention relies upon imaging the retinal vasculature of an individual animal to create the identifying record. Imaging the retinal vasculature provides a unique, unchanging, permanent, inexpensive, and unalterable method of identifying individual animals. Moreover, the method is equally effective on the eyes of living or recently dead animals.

Figure 7:
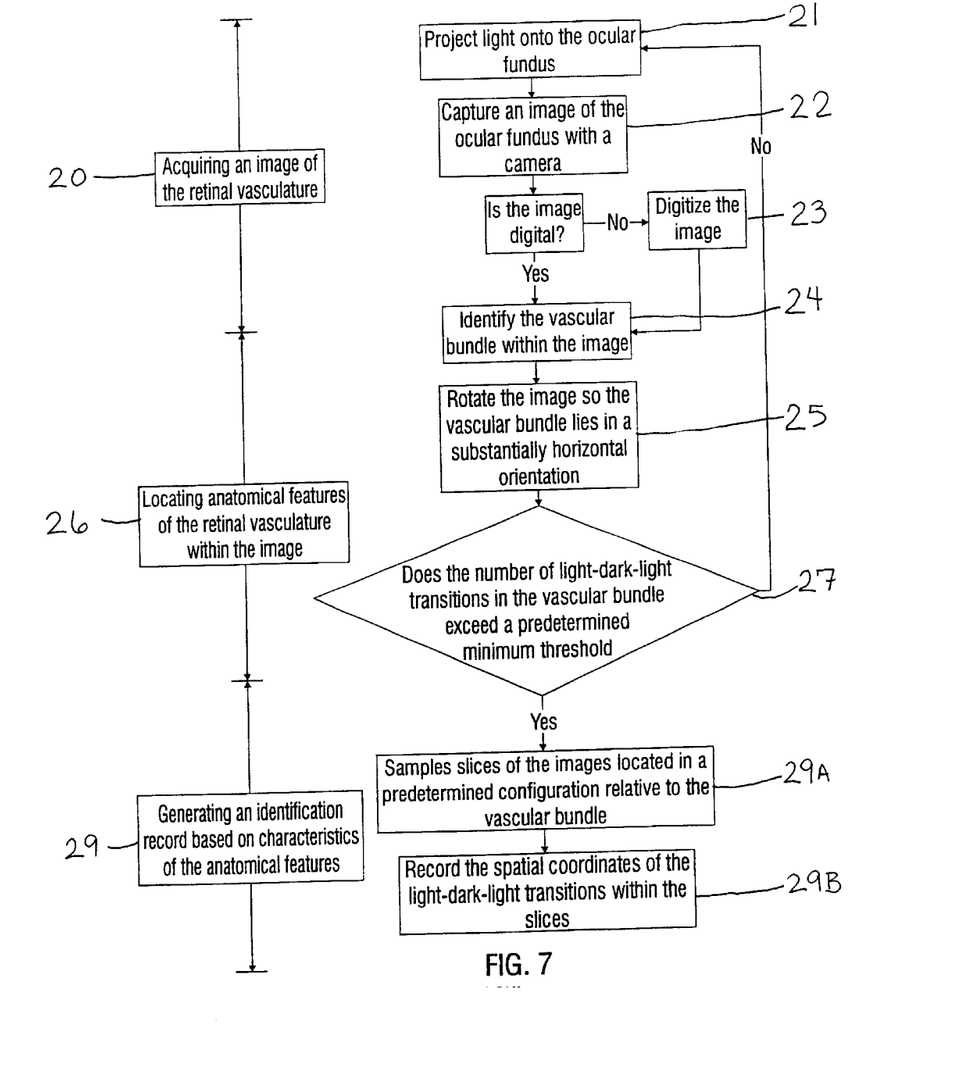
FIG. 7 is a flowchart of a method of identifying and analyzing the retinal blood vessels within the ocular fundus.

The method of the present invention creates a permanent record of an animal through a series of steps including, preliminarily acquiring an image of the retinal vasculature (box 20. FIG. 7) of the animal of interest; digitizing that image (box 23, FIG. 7) if the image is not a digital image; analyzing the image to determine if the image is satisfactory for further analysis; storing the image; and analyzing the image for unique anatomical landmarks. The image and data gathered therefrom may be stored in a database for later retrieval and comparison against other images. The data gathered from the image may be compared against other stored data in the database to determine the identity of the animal, assuming that data has previously been gathered and stored on the same animal.

In an effort to increase the dependability of the data gathered and to reduce fraud and misrepresentation regarding the identity of an animal, when the digital image is confirmed as acceptable and acquired for further analysis, the latitude and longitude of the place where the image is created and the satellite set real time may be recorded along with the image.

The retinal imaging system of the present invention would likely include an imaging device, for example a digital camera and a conventional personal computer. Preferably, the system would also include a global positioning system ("GPS") device which would simultaneously time and date stamp the acquired image as well as stamp the image with the location where the imaging took place by recording the latitude and longitude of that location.

BRIEF DESCRIPTION OF THE DRAWINGS

The foregoing and other advantages of the invention will become apparent upon reading the following detailed description and upon reference to the drawings in which.

DETAILED DESCRIPTION OF THE INVENTION

For the purposes of the present invention, "animal" means a human or animal, include those having a holangiotic eye. A holangiotic eye is an eye having vasculature on the ocular fundus, with the vasculature entering the eye, primarily through the optic nerve head. Virtually all domestic animal species (with the exception of the horse) and many game animal species, including deer and elk, have holangiotic eyes.

Using the method of the present invention, a "fingerprint" is made of the subject animal's retinal vasculature and stored in a database. That "fingerprint" can then later be used to positively identify the same animal when "fingerprinted" again.

The validity of this method is based on the infinite variability that exists with respect to certain anatomical landmarks of the retinal vasculature. Use of digitized image information regarding the retinal vascular pattern for individual identification is applicable in those animals having holangiotic eyes. These animal species have a vascular pattern that consists of arterioles and venules originating and resuming to the optic nerve head or disk. Horses do not have holangiotic eyes nevertheless, the method of the present invention is an effective means for identifying horses.

By targeting common structures such as the optic disk and dorsal retinal vascular branches, a consistent source of readily identifiable, yet contrasting structures are available for digital imaging and processing. Potential sensitivity and specificity of this system is very high since the precise vascular pattern geometric arrangement is unique between individuals. However, enough common features exist within species and breed groups that subcategorizing the data may be feasible to avoid the need to search an entire data set of all animals within the system.

Figure 1:
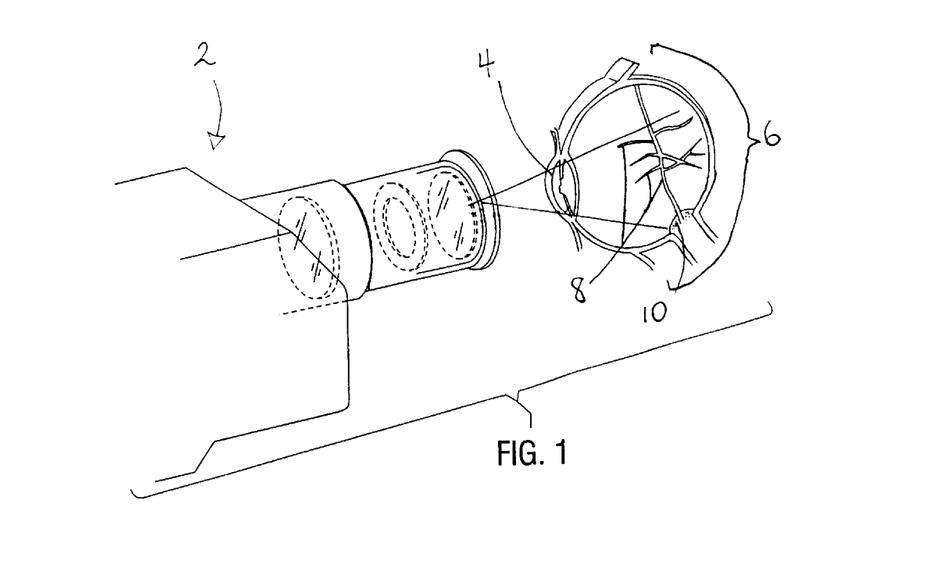
FIG. 1 is an illustration of an image acquisition device projecting light through the pupil of an animal's eye onto its ocular fundus.
Figure 2:
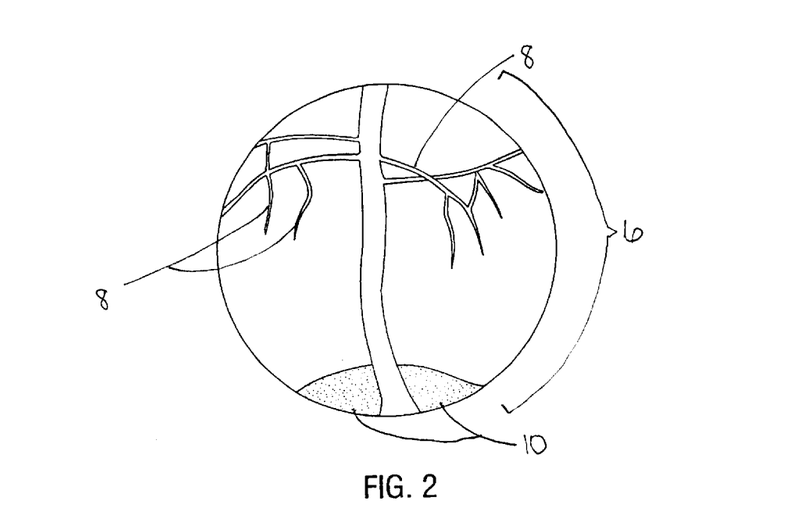
FIG. 2 is an illustration of a representative image of an animal's retinal vasculature showing the anatomical landmarks of interest.

FIG. 1 illustrates an image acquisition device 2 projecting light through the pupil 4 of the animal onto the animal's ocular fundus 6 so that an image may be acquired. As seen in FIG. 1, the ocular fundus 6 is the back of the inside of the eye opposite the pupil. Anatomically, the ocular fundus 6 consists of the majority of retinal blood vessels 8, optical disk 10, tapetum lucidum, retinal pigment epithelium (retina), and choroid pigment. FIG. 2 indicates this anatomy as viewed via the image acquisition device. The tapetum lucidum is a reflective layer in the ocular fundus 6 and provides excellent contrast to the overlying retinal blood vessels 8. The tapetum is generally present above the optic disk 10 in most animals. Humans and pigs do not have a tapetum, but the ocular fundus in these animals provides a high contrast background against which the vascular bundle can be imaged and detected.

The method of the present invention focuses on identifying and analyzing the vascular bundle of the retinal blood vessels 8 extending across the ocular fundus 6 from the optical disk 10 which is where the optic nerve leaves the retina. These blood vessels and their branches, which can exist infinite variations, offer a unique identifying attribute of the subject animal. Therefore, by accurately recording and analyzing the configuration of the blood vessels 8, the subject animal can be positively identified.

The method of acquiring and image of at least a portion of an ocular fundus according to the present invention is different from those traditional retinal scanning methods generally used to identify individuals for security purposes that operate similar to bar code scanners. That is, they scan the inside of the eye, without capturing an image of it, looking for light-dark-light patterns similar to a bar code. Such methods are not as exacting as the method of acquiring an image of at least a portion of an ocular fundus according to the present invention and are thus not as accurate, either. Furthermore, the method of acquiring an image according to the present invention allows for the construction of libraries of images, while scanning methods do not have this capability. Besides identification purposes, these libraries may be able to be used for the evaluation of health changes in the animal that are manifested in retinal changes, for example diseases associated with Vitamin A and degenerative vascular conditions. Certain physiological states, such as pregnancy, may also be detected in the images resulting from the method of the present invention.

The methods of creating an identification record for identifying an animal, and associated apparatus and system, according to the present invention provide accurate results because the configuration of the retinal blood vessels 8 cannot be falsified or altered. Thus, the pattern of retinal blood vessels 8 offers an incredibly accurate, unalterable, and unchanging characteristic of the subject animal which can be relied on for identification purposes.

The apparatus of the present invention includes a means for capturing an image of the target retinal vasculature. For example, a digital camera, video camera, or camera using a charge coupled device ("CCD") would be acceptable. An exemplary device would be a SONY DSC-F1 with a 640× 480 CCD imaging chip with infrared capability.

Affixed to the device used to acquire the image of the retinal vasculature would preferably be a lens that directs light (either infrared, low red, or visible) into the eye and allows a majority of the vascular bundle to be visualized.

This type of lens system would be similar to a lens such as that used on a conventional ocular fundus camera. The lens could be a wide angle or "fish-eye" lens. Preferably, however, the lens would be a 100° to 120° angle, wide angle lens. The means by which light may be directed into the eye is not critical. Preferably, light would be directed into the eye by a ring light or other light source coupled to the lens.

The apparatus of the present invention would also preferably include a microprocessor and storage media. For the purposes of the present invention, "storage media" is defined as any acceptable means for electronically storing images and data including CD, disk, tape, "smart card", and the like. The microprocessor could be in the form of a stand alone personal computer ("PC"), or more preferably, would reside within the same housing as the device used to acquire an image of the retinal vasculature. The device used to acquire the image would preferably be a handheld, self-contained unit. In that case, the device would also include a means for inputting information and a means for viewing images and related information. Nonetheless, the device need not be handheld or self-contained to be acceptable for the purposes of the present invention. If a stand alone PC would be used, the device used to acquire the image of the target retinal vasculature could transfer data to the PC by any means, for example by infrared port, PC card, magnetic media (e.g., disk, CD, or tape), or cable.

Preferably, a GPS receiver would be used in conjunction with the device for acquiring an image of the animal's retinal vasculature. While the use of a GPS receiver in conjunction with the device for acquiring an image of the animal's retinal vasculature is not necessary for the performance of the steps of acquiring an image of at least a portion of an ocular fundus, extracting anatomical structure data therefrom, or collecting biometric information or measurement according to the present invention, the GPS receiver provides certain additional information which makes the record created of the animal's retinal vasculature more dependable and more difficult to falsify. The reason for this is that it would be almost impossible to falsify the identity of an animal if the initial and all later imaging records were accompanied by a location and time stamp as provided by a GPS receiver. The GPS receiver provides longitude and latitude data on the location where the record would be created accurate to within three meters. Presently, there is no known method to override or falsify this information because the GPS position data and other information would be encrypted. Preferably, all initial and all later identification records would be transmitted to a central control database where that information would be stored and be retrievable.

By accompanying an identification record with a GPS stamp including the location and time, the subject animal would essentially be assigned an address as is done with humans thus making it much more difficult for the identity of similar animals to be confused. Indeed, from the perspective of food safety, this accuracy is critical for identifying the source of a contaminant and other potentially infected animals and people who may have been exposed to the infected animal. For food safety purposes, it is important to be able to positively identify not only the animal, but also to be able to trace its previous locations. By including a GPS stamp with each identification record created, each previous location where an identification record was created on the animal would be identified in a manner that is virtually incontrovertible.

Assuming that all initial identification records and subsequent identification records are maintained in a central database, the records could be compared to determine the exact time and location of the last record taken on that individual. In essence, by combining a GPS receiver with the device for acquiring an image of the animal's retinal vasculature, the method of the present invention creates the equivalent of a social security identification system for animals. Because the information is so accurate, particularly with respect to the location of the animal at a precise time, cattle movements could be evaluated in near real time. Such information could have a stabilizing effect on commodity markets.

Furthermore, additional data could be added to the identification record by any known means, including audio recording, photographic record, digital encryption, and the like in the form of photographs of the animal and/or a feature or features of the animal; descriptions of the subject animal; birth or death dates of the animal; genetic breeding data; cause of death; the medical/veterinary records of the animal including, data about past medical/veterinary treatment including programmed future required or necessary treatment; feed formulas; feedlot locations: border crossings; shipping data and locations; ownership transfers; purchaser required information, e.g., registration certificates; purchaser desired auction information; slaughter and packing company locations; distribution locations; and the like. With respect to identification of humans, any information deemed appropriate and allowed by law could be a part of the identification record.

Additionally, the images could be assigned unique barcodes for each animal on which an identification record was generated. In the case of an animal sent to slaughter, such bar-code information could be used in a slaughterhouse or packing plant to identify parts of the animal as it proceeds through the meat packing process. Thus, any separate cut of meat, no matter where sold, could be accurately and easily traced back to the original animal based on the bar code.

Analysis of acquired images would occur either on board the device used to acquire the image or on the PC. Once a set of images has been accepted, analyzed, and the images and data stored electronically in storage media, the images and data may be transferred to a central location for further analysis and storage in a central database. The images and data may be communicated or transmitted by any acceptable means of communication, for example over the Internet, by satellite communication, by facsimile, and the like. Images and data may be communicated to the central location allowing for near real time further processing. The transfer could occur via any acceptable means of real time, high-speed data transfer.

The method of the present invention includes the step of preliminarily acquiring an image of the retinal vasculature (for reference see the box labeled 20, FIG 7) of the subject animal. One embodiment of the method is illustrated in the flowchart of FIG. 7. For the purposes of this invention, virtually any animal with a holangiotic eye, including a human, would be an acceptable subject for the practice of the method. As stated above, the method of the present invention provides acceptable results on the eyes of both live and recently dead animals. The subject animal would be presented for evaluation. The evaluation may take place virtually anywhere because the device for acquiring an image of the animal's retinal vasculature is extremely portable and because of the evolution of rapid communication for the transfer of data. Nonetheless, the method of the present invention would be most likely carried out at a location where the animal would be most easily managed, for example, at a medical clinic, at an on-farm working facility, at a veterinary clinic, at a feedlot, at a zoo, or similar facility.

Figure 3:
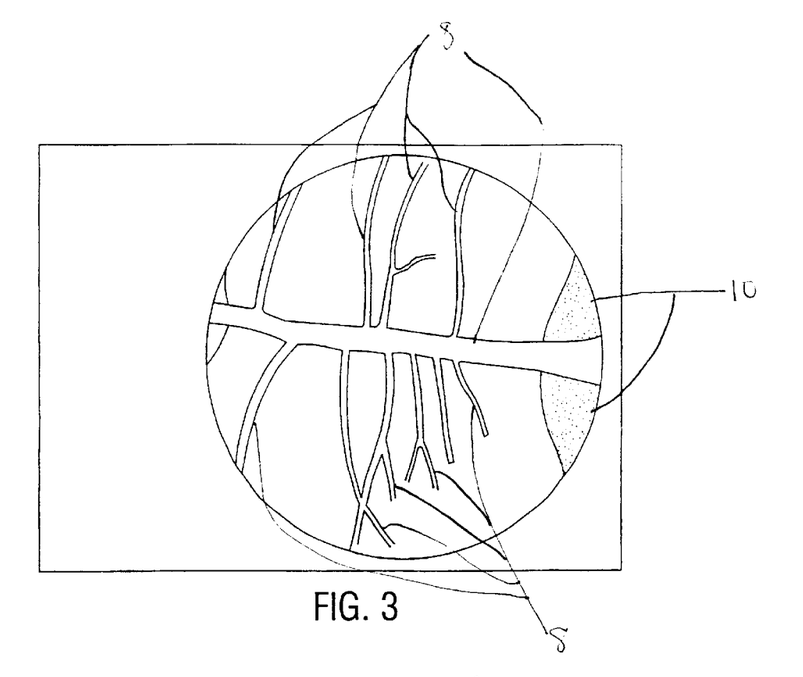
FIG. 3 is an illustration of an acquired image of a cow's retinal vasculature.

The animal would be positioned relative to the device. The device would be activated so that light (e.g., infrared, low red, or visible) is projected into the eye of the animal through the pupil and onto the ocular fundus (box 21, FIG. 7). An image of the animal's retinal vasculature would then be initially acquired by the image acquisition device (box 22 FIG. 7). This is illustrated in FIG. 1. A representative acquired image is illustrated in FIG. 3. One can readily note that the image in FIG. 3 is similar to that in FIG. 2 except that it has been rotated 90 degrees.

Once the image has been initially acquired, the image, if not a digital image, would be digitized (box 23 FIG. 7). Then, the image would be preliminarily analyzed to determine if that image would be satisfactory. The analysis performed on the image is to identify (box 24, FIG. 7) the vascular bundle of blood vessels 8, i.e., every generally visible artery and vein that runs across the retina from the optic disk 10.

This analysis is continued in a effort to locate anatomical features of the vasculature (box 26, FIG. 7.) using an object oriented algorithm which "slices" the image at an angle that is expected to be approximately perpendicular to the vascular bundle 8 when the device is held approximately level. The width of the slice (in pixels) and stride between slices may be varied as needed. The data in these slices would then be converted to a high contrast gray representation of the slice by averaging the red, green and blue octets of each pixel. Contrast may be adjusted by the user or may be set automatically. Each slice would then be tested for variation among the pixels. If sufficient variation exists, then the major transitions in the slice of light-dark-light pixels would then be detected using a moving average analysis. The number of pixels in the moving average may be varied as needed. The transition is detected by a threshold that is determined by the average pixel value in a larger moving average of pixels in the same slice (box 27, FIG. 7). This allows for detection in variable contrast sections of the slice and between slices.

Figure 4:
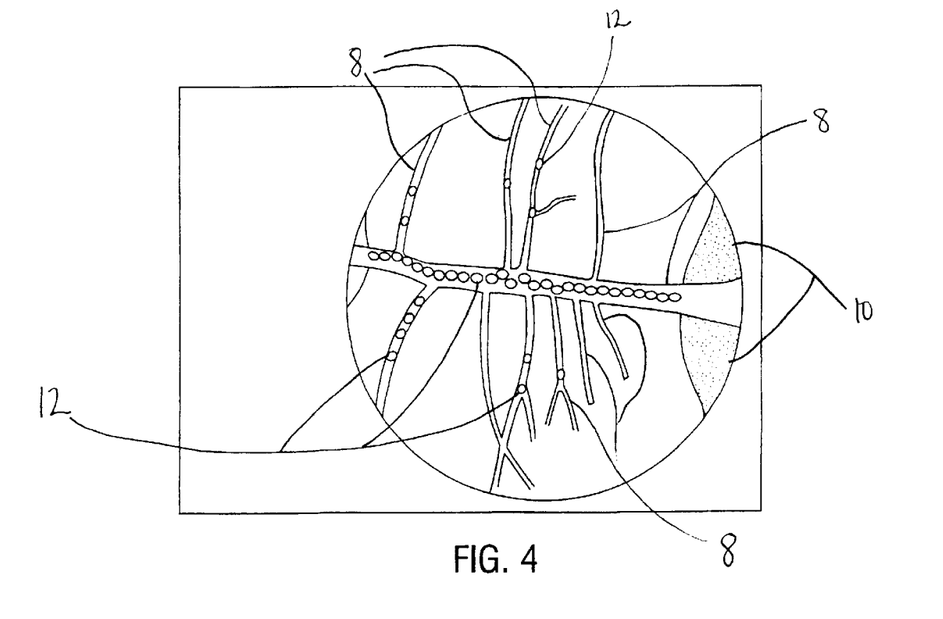
FIG. 4 is an illustration of the image of FIG. 3 wherein the light-dark-light transitions have been detected.

Referring to FIG. 4, when a light-dark-light transition is detected the location is marked by storing the coordinates (box 29B, FIG. 7) of the center of the group of contiguous pixels in the current moving average in a linked list. Exemplary locations of the center coordinates of groups of contiguous pixels are marked on the image illustrated in FIG. 4 as 12.

Figure 5:
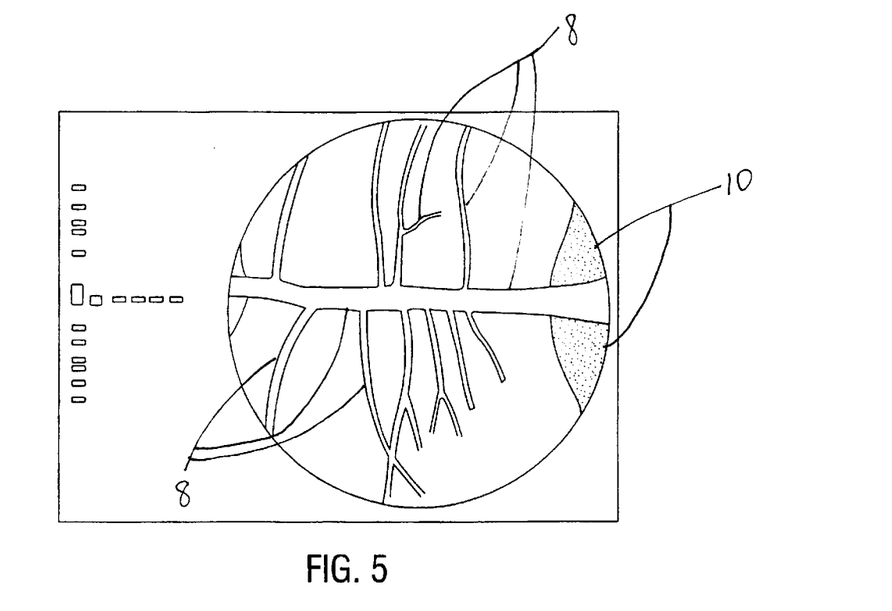
FIG. 5 is an illustration of the image of FIG. 3 wherein the image has been rotated and normalized.

When all slices of an image have been analyzed, the linked list of marked coordinates would be transferred to an algorithm that simultaneously normalizes the image and detects the coordinate of the axes produced by the vascular bundle 8 in the dimension the slices were taken. This analysis is accomplished by first performing a k-means cluster analysis in one dimension using the same dimension in which the slices were taken. The maximum number of clusters allowed may be varied as needed. The image would then be rotated (box 25, FIG. 7) about the center of the image using standard image rotation methods in the radian scale and the cluster analysis repeated. A search for the best rotation would then be performed. The rotation of the image where the largest cluster has the most points from the linked list is the acceptable angle for normalization. Other known methods for determining the angle of normalization may be used if desired. At normalization, the coordinates in the plane in which the slices were taken that is represented by the largest cluster is also the location of the vascular bundle 8 in the perpendicular plane. This result is illustrated in FIG. 5.

If after the preliminary analysis, the initially acquired image meets certain minimal criteria the image may be accepted by the operator. The operator then signals acceptance of the normalized image by saving the image and preliminary analysis in an electronic storage medium. The minimal criteria for acceptance are based on the number of contiguous marks on the vascular bundle 8 (the size of the largest cluster). The minimum criteria include (1) a minimum number of points in the maximum sized cluster (which may be varied as needed) and (2) no other cluster has more than a maximum number of points (which also may be varied as needed). The operator would indicate acceptance of the image by saving the image to the storage medium on board the device or on the PC to which the image acquisition device is coupled.

Preferably, at the time the image is saved, the accepted image would be simultaneously stamped with an encrypted record of information taken from an attached GPS receiver. The resulting saved image, preliminary analysis data, and other relevant information comprise an identification record (show generally as box 29, FIG. 7). Additional desired information could also be added, such as ownership, performance data, pedigrees, breed composition, and the like.

Once an identification record has been created, the image, preliminary analysis data, and information could be transferred to a stand alone PC, either at the site of the creation of the record or at a distant location, for additional analysis. Preferably, following the creation of the identification record, it would be transferred to a central location for additional analysis and storage in a database. The transfer of the information to the distant location could be done by any known means of communication, including transfer over phone lines, over the Internet, using satellite communication, by facsimile, and the like.

To review as depicted in FIG. 7, the preliminary analysis which the image undergoes includes a determination of the unique anatomical attributes of the retinal vasculature of the subject animal (show generally as box 26) and to generate an identification record (box 29). In these step, at least two slices of the image are identified for further processing, one on each side of the axis of the vascular bundle 8 detected in the preliminary analysis of the image. The width, number, and exact location of the slices may be varied as needed. The analysis of the slices results in the creation of a unique digital "fingerprint" of the animal's retinal vasculature.

Figure 6:
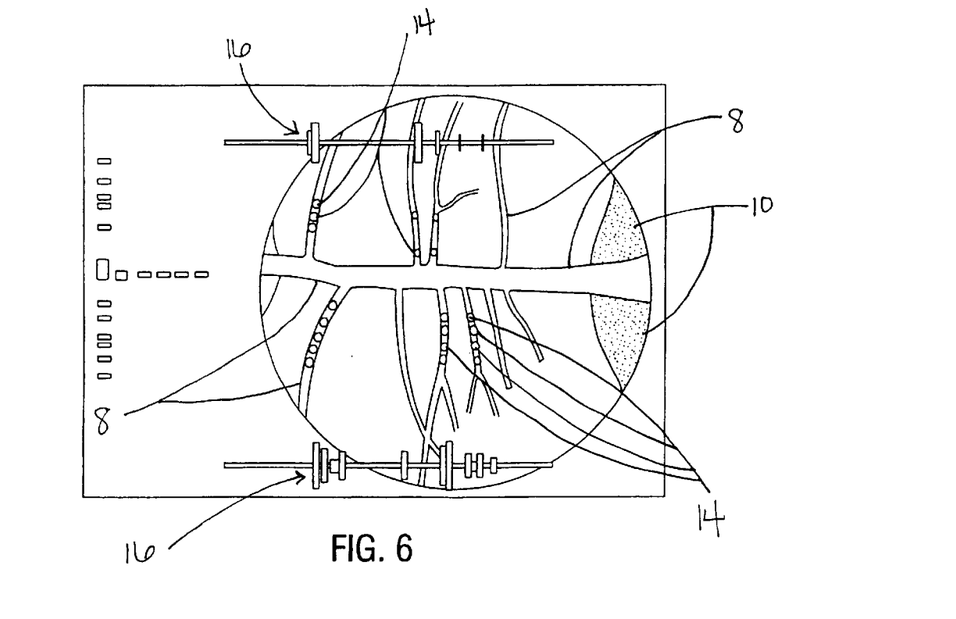
FIG. 6 is an illustration of the image of FIG. 3 wherein the unique anatomical landmarks of the particular animal's retinal vasculature have been detected so as to identify the subject animal.

The slices are analyzed for light-dark-light transitions which correspond to the blood vessels branching from the vascular bundle 8. The coordinates of each of these transitions would then be detected. Represented in FIG. 6 as tiny circular shapes, the coordinates of each light-dark-light transition detected 14 makes a unique pattern (the total detected strength of which is represented at (16) with a sufficient number of combinations to assure that animals will be uniquely identified. At this point, a unique identification record has been created for the subject animal.

For the purposes of using a database of this information for identifying a specific animal, the data gathered from a newly generated identification record would be compared with data in the database.

What is claimed is:

1. A method of creating an identification record for a non-human animal, the method comprising:

using a camera and a non-scanning illumination source, acquiring an image of at least a portion of an ocular fundus of the animal, using a microprocessor, extracting a set of analysis data from the acquired image representing a particular identified anatomical structure of the ocular fundus, generating information indicative of day and geographic location of the image acquisition, and generating the identification record to comprise at least the analysis data and the information.

2. The method of claim 1, wherein the step of acquiring an image comprises capturing the image with the camera, digitizing the image for storage, transmitting the digitized image to a computer, and the anatomical structure so represented is retinal vasculature.

3. The method of claim 1, wherein the step of extracting a set of analysis data comprises identifying and selecting the particular structure from the group of structures consisting of at least a portion of retinal vasculature and an optic disk, and characterizing sections of the acquired image that are located in a predetermined configuration relative to the identified anatomical structure; and the step of generating information further comprises receiving data with a Global Positioning System (GPS) receiver comprising the location and a time the image was so acquired.

4. The method of claim 1, wherein the step of extracting a set of analysis data further comprises rotating the acquired image so that the structure lies in a predetermined orientation.

5. The method of claim 4, wherein the step of extracting a set of analysis data further comprises:

sampling a plurality of sections of the acquired image that lie in predetermined locations relative to the structure, detecting a plurality of light-dark-light transitions within each of the sections, and identifying a coordinate location of each of the light-dark-light transitions so detected.

6. The method of claim 5, wherein each of the sections comprises a slice having a width and the step of extracting a set of analysis data further comprises storing a set of spatial coordinates for each of the transitions in a linked list, normalizing the acquired image comprising detecting an axis of the structure in a common dimension of the slices.

7. The method of claim 6, wherein the step of normalizing the acquired image further comprises, once the axis is detected, rotating the structure until a plane is identified that comprises a maximum total number of the transitions, whereby if a predetermined minimum threshold number of the transitions in the identified plane is met, the spatial coordinates representing the structure in the identified plane, is selected.

8. The method of claim 1, wherein the anatomical structure so represented is retinal vasculature, the identification record further comprises a time the image was so acquired, and the step of generating information further comprises receiving data comprising the location with a Global Positioning System (GPS) receiver.

9. The method of claim 8 further comprising the steps of: storing the identification record in a database comprising a plurality of prior-generated identification records; and generating a subsequent identification record for the animal comprising the step of gathering a subsequent set of biometric information comprising location, date, and time data received by the GPS receiver.

10. The method of claim 1, wherein the step of generating the identification record further comprises including additional data selected from the group consisting of audio data, visual data, a description of the animal, birth date of the animal, death date of the animal, genetic breeding data, production data, veterinary records of the animal, medical records of the animal, feed formulas, feedlot locations, border crossings, shipping data, ownership transfers, purchaser required information, a bar-code assigned to the animal, digital encryption, a photographic record of the animal, microchip implant data, and Global Positioning System (GPS) data received by a GPS receiver.

11. The method of claim 1, wherein the animal is dead.

12. A method of identifying a non-human animal, the method comprising:

extracting a first set of biometric information from an acquired image of at least a portion of an ocular fundus of the animal, the image having been acquired using a camera and a non-scanning illumination source generating information indicative of day and geographic location of the image acquisition, generating an initial identification record comprising at least a portion of the first set of biometric information, the information indicative of day and geographic location, and an identity of the animal, storing the initial identification record in a database, the database comprising a plurality of previously stored identification records, gathering a subsequent set of biometric information from the animal, generating a subsequent identification record comprising the subsequent set of biometric information, and determining the identity of the animal by:

comparing the biometric information in the subsequent identification record to the biometric information in each of the previously stored identification records in the database, and if a matching identification record is found in the database, extracting the identity of the animal therefrom.

13. A method of creating an identification record for a non-human animal, the method comprising:

employing a Global Positioning System (GPS) receiver to receive GPS data comprising at least a day and geographic location of the animal at the time a biometric measurement therefor is collected, the biometric measurement comprises an image, generated using a camera and a non-scanning illumination source, of at least a portion of an ocular fundus, and storing at least the GPS data and the biometric measurement as the identification record.

14. The method of claim 13, wherein the identification record further comprises a second measurement selected from the group consisting of an audio recording, a still photograph of at least a feature of the animal, a moving photograph of at least a feature of the animal, a measurement concerning genetic breeding, an image of at least a portion of an anatomical feature of the animal, a DNA test measurement, a measurement taken in connection with medical treatment, a reading from a microchip implanted in the animal, and a disease screening test.

15. The method of claim 14, wherein the portion of an ocular fundus comprises at least a portion of retinal vasculature, and the step of employing a GPS receiver further comprises receiving a time for the biometric measurement.

16. An apparatus for creating an identification record for a non-human animal, the apparatus comprising:

an image acquisition device for capturing an image of at least a portion of an ocular fundus of the animal, the device comprising a non-scanning illumination source for projecting light onto the ocular fundus of the animal and a camera;

a computerized image analysis device for extracting a set of analysis data from the acquired image, the analysis data to represent a particular identified anatomical structure of the ocular fundus; and a device for receiving data indicative of day and geographic location of the animal when the image was so acquired.

17. The apparatus of claim 16, wherein the animal is dead, the anatomical structure so represented is at least a portion of retinal vasculature and the device for receiving data comprises a Global Positioning System (GPS) receiver.

18. The apparatus of claim 17, wherein the non-scanning illumination source for projecting light onto the ocular fundus of the animal comprises an infrared light source and a lens system contained within a single housing, the image acquisition device and device for receiving data are interfaced, and the GPS data further comprises a time the image was so acquired.

19. A system for identifying a non-human animal, the system comprising:

a computerized image analysis device for extracting first biometric information from an image of at least a portion of an ocular fundus of the animal;

an image acquisition device comprising a camera and a non-scanning illumination source;

a storage device for storing an identification record, the identification record comprising the first biometric information, information indicative of day and geographic location of acquisition of the image, and an identity record of the animal; and a processor for comparing the first biometric information to a plurality of identification records, each comprising biometric information and an animal identity previously stored, to find a matching identification record.

20. The system of claim 19, wherein the processor for comparing resides on a second computer at a location distant from the computerized image analysis device, and the identification record of the animal is transmitted to the processor over a communication means selected from the group consisting of infrared signal transmission, network cable, telephone line, internet, satellite transmission, or facsimile transmission.

21. The system of claim 19, wherein the information indicative of day and geographic location comprises Global Positioning System (GPS) data received by a GPS receiver and the storage device comprises media selected from the group consisting of compact disk (CD), magnetic disc, optical disc, magnetic tape, or smart card.

22. The system of claim 19, wherein the storage device comprises a device that stores information electronically, and the information indicative of day and geographic location comprises Global Positioning System (GPS) data further comprising a time the image is acquired.

23. The system of claim 19, wherein the storage device for storing the identification record is interfaced with a computer, the identification record of the animal is transmitted to the processor for the comparing, and the animal is dead.

24. The system of claim 23, wherein the first biometric information is transmitted to the computer by means selected from the group consisting of an infrared port, PC card, magnetic media, and cable; and the storage device comprises media selected from the group consisting of compact disk, magnetic disc, optic disc, magnetic tape, or smart card.

25. A system for identifying a non-human animal, the system comprising:

means for gathering biometric information about the animal, said means comprising a camera and a non-scanning illumination source for acquiring an image of at least a portion of an ocular fundus of the animal;

means for storing an identification record, the identification record comprising the biometric information, information indicative of day and geographic location of acquisition of the image, and an identity record of the animal, whereby a plurality of previously stored identification records, each comprising biometric information and an animal identity form a database; and means of comparing the identification record for the animal to the plurality of stored identification records in the database to find a matching identification record, and extracting the identity of the animal from the matching identification record.

\* \* \* \* \*